United States Patent
Kumagai et al.

(10) Patent No.: US 7,850,834 B2
(45) Date of Patent: Dec. 14, 2010

(54) ELECTROPHORESIS METHOD USING CAPILLARY PLATE

(75) Inventors: Hidesato Kumagai, Kyoto (JP); Shin Nakamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1078 days.

(21) Appl. No.: 11/360,674

(22) Filed: Feb. 24, 2006

(65) Prior Publication Data

US 2006/0201808 A1 Sep. 14, 2006

(30) Foreign Application Priority Data

Mar. 9, 2005 (JP) .............................. 2005-065547

(51) Int. Cl.
*G01N 27/447* (2006.01)
(52) U.S. Cl. ....................... 204/451; 204/601
(58) Field of Classification Search ................ 204/451, 204/452, 455, 601, 602, 607, 608, 606
See application file for complete search history.

(56) References Cited

U.S. PATENT DOCUMENTS

| | | | |
|---|---|---|---|
| 5,037,523 A * | 8/1991 | Weinberger et al. | ......... 204/602 |
| 5,458,761 A | 10/1995 | Kamahori et al. | |
| 6,682,641 B1 * | 1/2004 | Finney et al. | ............... 204/466 |
| 2003/0102219 A1 * | 6/2003 | Yamamoto et al. | .......... 204/600 |
| 2003/0127328 A1 * | 7/2003 | Nordman et al. | ............ 204/451 |

FOREIGN PATENT DOCUMENTS

| | | |
|---|---|---|
| ES | 20788787 A1 | 12/1995 |
| JP | 61278752 A | 12/1986 |
| JP | 08211018 A | 8/1996 |
| JP | 2002-310990 | 10/2002 |
| JP | 2003-166975 | 6/2003 |

OTHER PUBLICATIONS

Anal. Chem. 2000, 72, 3129-3137; Optimization of High-Performance DNA Sequencing N Short Microfabricated Electrophoretic Device; Oscar Salas-Solano, Dieter Schmalzing, Lance koutny, Scott Buonocore, Aram Adourian, Paul Matsudaira, and Dan Ehrlich.

* cited by examiner

*Primary Examiner*—Nam X Nguyen
*Assistant Examiner*—Gurpreet Kaur
(74) *Attorney, Agent, or Firm*—Manabu Kanesaka

(57) ABSTRACT

In an electrophoresis method, a capillary plate having a capillary channel is maintained in a predetermined temperature to be processed, and a sample is filled into the capillary channel. A solution is prepared to have a temperature substantially the same as the predetermined temperature of the capillary plate, and the solution is injected into the capillary channel maintained in the predetermined temperature. Voltage is applied between two ends of the capillary channel to perform electrophoresis of the sample.

5 Claims, 5 Drawing Sheets

ELECTROPHORESIS METHOD USING CAPILLARY PLATE

BACKGROUND OF THE INVENTION AND RELATED ART STATEMENT

The present invention relates to an electrophoresis method, for separating and analyzing samples by electrophoresis using a capillary plate having capillary channels, in order to analyze very minute quantities of samples, such as proteins and amino acids, drugs, and the like, in the fields, such as biochemistry, molecular biology, and clinical practice.

Electrophoresis devices have been used from the past when analyzing very minute quantities of proteins and amino acids, and the like. There is a capillary electrophoresis having capillary tubes as a representative thereof. However, the handling of a device having capillary tubes is complicated. Therefore, a capillary plate having plural capillary channels formed inside a substrate has been proposed and used with the purpose of making the handling easier and also for acceleration of analysis and miniaturization of the device (see Patent Documents 1 and 2).

In the capillary plate, the capillary channels serve as separation channels for electrophoresis, and both ends are opened on the substrate surface. The openings on one end side serve as sample reservoirs for sample injection. In electrophoresis using a capillary plate (below, called also capillary electrophoresis), a separation medium is packed into the capillary channels; then samples are injected from the sample reservoirs; then a solution is injected into those reservoirs; and then voltage is applied between the two ends of the capillary channels to perform electrophoresis of the samples.

Also, it may have a process such that after packing of the separation medium into the capillary channels, the solution is injected into the reservoirs before injection of the samples, and then voltage is applied between both ends of the capillary channels to perform preprocessing.

In capillary electrophoresis, the temperature of the capillary plate itself is regulated (temperature-regulated) for improvement of its separation performance. However, the solution filled into the reservoirs during preprocessing for electrophoresis or during electrophoresis of the samples was not particularly temperature-regulated before injection. Normally, it was injected into the reservoirs in a room-temperature (normal-temperature) state, and the solution inside the sample reservoirs was temperature-regulated by temperature-regulating the capillary plate itself.

Patent Document 1: Japanese Unexamined Patent Publication No. 2002-310990
Patent Document 2: Japanese Unexamined Patent Publication No. 2003-166975
Non-Patent Document 1: Anal. Chem., 2000, 72, 3129-3137

Regardless of whether the capillary plate is temperature-regulated for improvement of separation performance, there is a phenomenon that the improvement of separation performance is not sufficiently achieved.

The present invention has been made to further improve the separation performance when performing electrophoresis by temperature-regulating the capillary plate.

Further objects and advantages of the invention will be apparent from the following description of the invention.

SUMMARY OF THE INVENTION

Methods for improving the separation performance have been studied. As a result, the capillary plate was often temperature-regulated to become in a high-temperature state, and therefore, when room-temperature solution was injected into the sample reservoirs after packing the separation medium into the channels, the heat was absorbed from the capillary plate, and the separation medium inside the channels contracted or expanded accompanying the temperature change. It was discovered that this is the cause of lowering of separation performance. In particular, the lowering of separation performance was prominent in the case when the separation medium contracted or expanded after sample injection.

Therefore, the present invention has been made so as to prevent the lowering of separation performance by preventing contraction or expansion of the separation medium.

That is, the present invention takes as subject an electrophoresis method, wherein a capillary plate having capillary channels is used, a separation medium is packed into the capillary channels, then samples are injected from reservoirs on one end of the capillary channels, then a solution is injected into those reservoirs, and then voltage is applied between the two ends of the capillary channels to perform electrophoresis of the samples, wherein the capillary plate is maintained at a constant temperature, and the solution is injected into the reservoirs in a state being maintained at a temperature substantially the same as the maintained temperature of the capillary plate.

By injecting into the reservoirs the solution maintained at a temperature substantially the same as the maintained temperature of the capillary plate, the temperature change caused in the separation medium inside the capillary channels and the contraction or expansion of the separation medium are reduced, whereby lowering of the separation performance is suppressed.

Accordingly, "temperature substantially the same as the maintained temperature of the capillary plate" means that the temperature of the solution is a temperature near enough to the maintained temperature of the capillary plate such that the temperature change caused in the separation medium and the contraction or expansion of the separation medium are reduced. As for such temperature, by making the temperature of the solution preferably ±5 degrees, and more preferably ±2.5 degrees, with respect to the maintained temperature of the capillary plate, it is possible to suppress lowering of the separation performance.

The present invention is also directed as subject to a method having a process wherein after packing of the separation medium into the capillary channels, the solution is injected into the reservoirs before injection of the samples, and then voltage is applied between both ends of the capillary channels to perform preprocessing. In that case, it is preferable that the solution injected for preprocessing is also injected into the reservoirs in a state being maintained at a temperature substantially the same as the maintained temperature of the capillary plate.

One example of the capillary plate used in the invention has plural capillary channels, and the reservoirs consist of a common large-capacity reservoir provided on the sample injection side of the plural capillary channels, and small-capacity reservoirs provided for each of the respective capillary channels at the bottom of that large-capacity reservoir. In that case, the samples are injected into the small-capacity reservoirs, and the solution is injected into the large-capacity reservoir.

In the present invention, because the temperature of the solution injected into the reservoirs during electrophoresis of the samples is made substantially the same temperature as the maintained temperature of the capillary plates, the temperature change caused in the separation medium inside the capillary channels is prevented, and the contraction or expansion of the separation medium is reduced, whereby the lowering of separation performance can be suppressed.

BRIEF DESCRIPTION OF THE DRAWINGS

FIGS. 1(A)-1(D) are drawings showing one example of a capillary plate in which the present invention is applied, wherein FIG. 1(A) is a plan view of the capillary channels, FIG. 1(B) is an enlarged plan view of the sample reservoir (small-capacity reservoir) part on the cathode end, FIG. 1(C) is a perspective view of the cathode end, and FIG. 1(D) is a sectional view of the cathode end;

DETAILED DESCRIPTION OF PREFERRED EMBODIMENTS

Figure 1A:
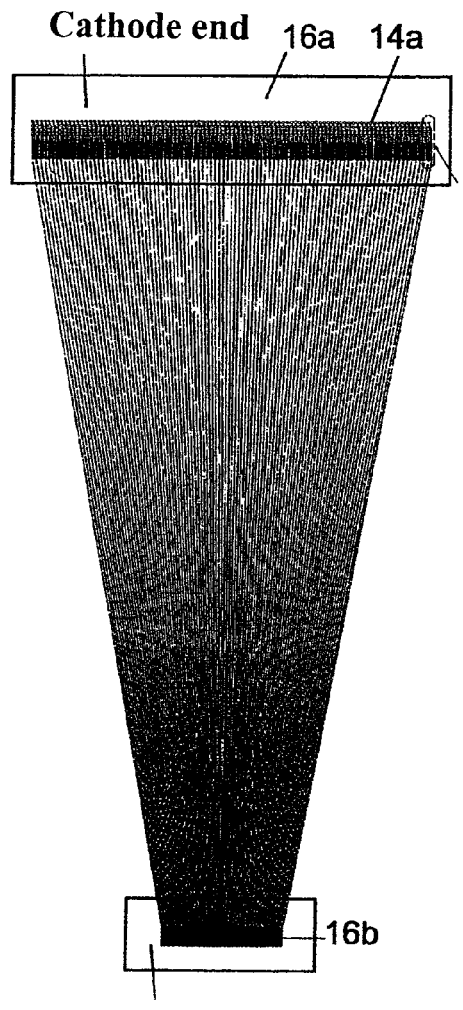

Below, a working example of the present invention, which uses a MEMS (Micro Electro Mechanical System) capillary plate as electrophoresis member, is explained in detail while referring to the drawings.

Figure 1B:
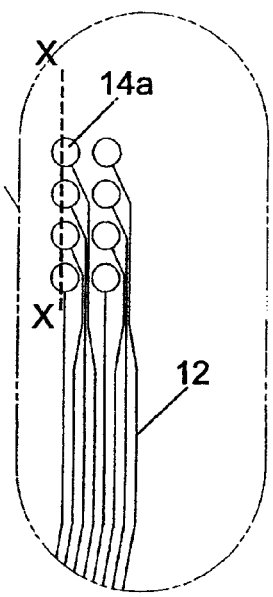
Figure 1C:
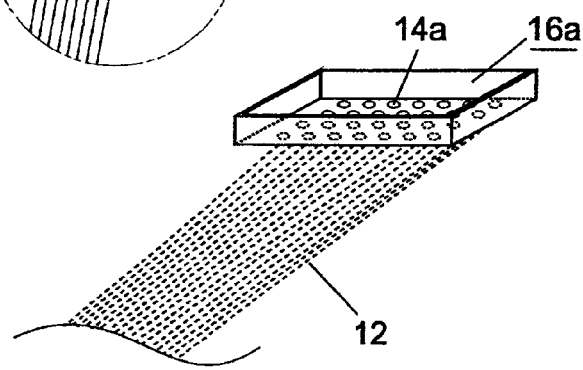
Figure 1D:
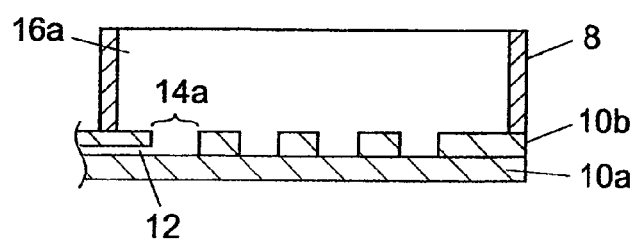

In FIGS. 1(A) to 1(D), FIG. 1(A) is a plan view of the capillary channels in the capillary plate, FIG. 1(B) is an enlarged plan view of the sample reservoir (small-capacity reservoir) part on the cathode end, FIG. 1(C) is a perspective view of the cathode end, and FIG. 1(D) is a sectional view of the cathode end.

The capillary plate has a pair of plate members 10a, 10b bonded together. On one plate member 10a, plural, for example 384, separation channels 12 consisting of capillary channels are formed, and they are arranged so as not to intersect with each other.

One end (cathode end) of each separation channel 12 is connected to a small-capacity reservoir 14a which is a sample reservoir opened on the substrate surface, and on the substrate surface, a large-capacity reservoir 16a having a size containing all the small-capacity reservoirs 14a is formed to be surrounded by a wall 8. The other end (anode end) of each separation channel 12 is opened so as to be connected to a common reservoir 16b formed on the substrate surface.

The width of the separation channel 12 is 100~1000 μm, preferably 50~90 μm, and the depth is 100~1000 μm, preferably 20~40 μm. On the other plate member 10b, through-holes are formed in positions corresponding to the two ends of the separation channels 12. As the size of the small-capacity reservoir 14a, it has a diameter of 10 μm~3 mm, preferably 50~m~2 mm, and it is set to a size suitable for injecting several 10 nL ~several μL of sample. Both plate members 10a and 10b are affixed together with the separation channels 12 on the inside to become a single plate member.

Formation of the separation channels 12 on the plate member 10a can be done by lithography and etching (wet etching or dry etching). Formation of the through-holes on the plate member 10b can be done by a method such as sand blasting or laser drilling.

The entire area of the small-capacity reservoirs 14a is covered by the large-capacity reservoir 16a, and as in shown in FIG. 1(C) showing the perspective view, all the small-capacity reservoirs 14a are provided inside the large-capacity reservoir 16a, and they are connected with the reservoir 16a. The reservoir 16b on the other end side also covers the area where the openings on the other end side of all the separation channels 12 are disposed, and the openings on the other end side of all the separation channels 12 are connected with the reservoir 16b.

As for the material of the plate members 10a, 10b constituting the substrate, quartz glass or borosilicate glass, resin, or the like, can be used, and a transparent material is selected in the case when the components separated by phoresis are detected optically. In the case when using a detecting means other than light, the material of the plate members 10a, 10b is not limited to transparent plate.

The inner wall of the small-capacity reservoir 14a may be made hydrophilic, and the bottom of the large-capacity reservoir 16a or from the bottom to the inner wall may be made hydrophobic. As for the surface treatments for such hydrophilic and hydrophobic properties, various methods can be mentioned. For example, in the case of using a glass plate as the plate member, the hydrophilic property can be given by acid treatment, and the hydrophobic property can be given by coating with resin, processing with fluorine resin or treating with silane coupling agent.

Figure 2:
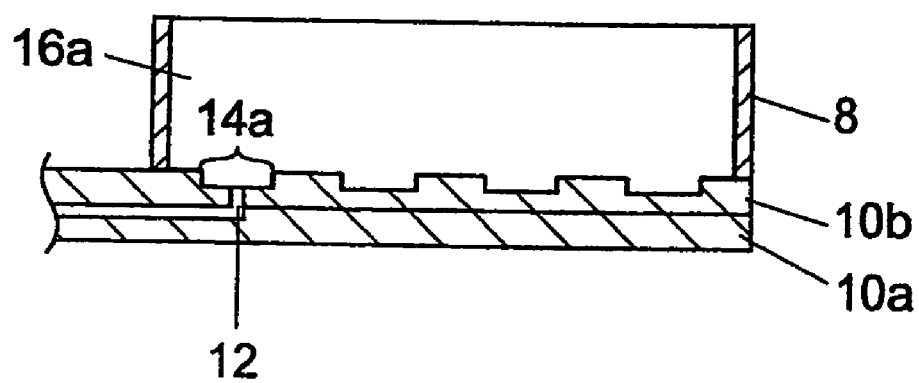
FIG. 2 is a sectional view of an end on the cathode side of another capillary plate.

FIG. 2 shows a sectional view on the cathode side of the another capillary plate. The small-capacity reservoir 14a is formed as a cavity on the surface side of the plate member 10b, and it is connected at the bottom with the separation channel 12. Plural small-capacity reservoirs 14a are covered by a large-capacity reservoir 16a, and they are formed on the bottom of the large-capacity reservoir 16a.

Figure 3:
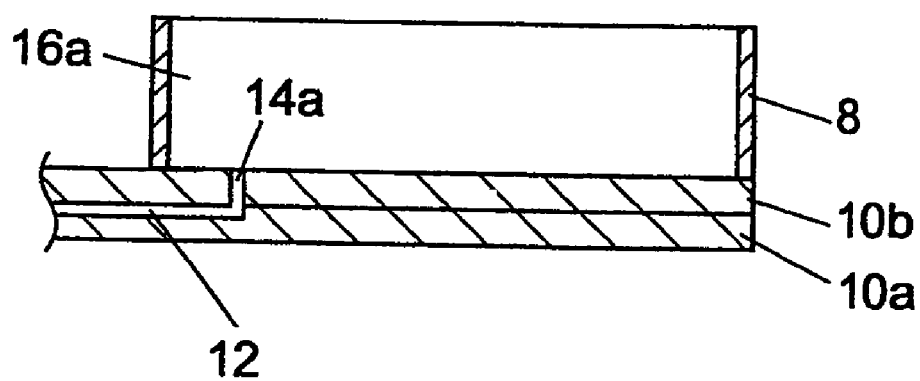
FIG. 3 is a sectional view of an end on the cathode side of yet another capillary plate.

FIG. 3 shows a sectional view on the cathode side of yet another capillary plate. The small-capacity reservoir 14a is formed as an opening having a size about the same extent as the separation channel 12.

In either of these capillary plates shown in FIG. 2 or FIG. 3, surface treatment may be applied so that the small-capacity reservoir 14a and a narrow range of the periphery of the opening of the small-capacity reservoir 14a on the bottom of the large-capacity reservoir 16a become hydrophilic, and the outside of that becomes hydrophobic. By this treatment, the injected sample comes to be held in the part applied with the hydrophilic treatment, and that hydrophilic area becomes the small-capacity reservoir. The size of that hydrophilic area is set to a size suitable for the quantity of sample held to become several 10 nL~several ~L.

Next, the sample injection operation in the capillary plate in FIGS. 1(A) to 1(D) is explained while referring also to FIGS. 4(A) to 4(D).

(1) The capillary plate 10 is kept in a constant-temperature state of 50° C. This constant-temperature state is maintained until electrophoresis of the sample ends.

Figure 4A:
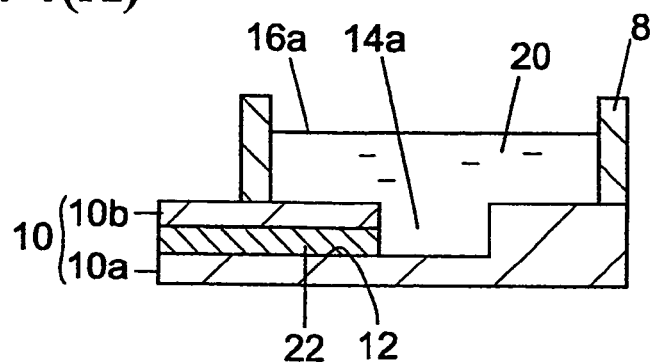
FIGS. 4(A)-4(D) are sectional views of the process showing the operation of one working example.

(2) As shown in FIG. 4(A), the large-capacity reservoir 16a on the cathode side is filled with pure water 20, for example Milli-Q water which is ultra-pure water, and gel 22 which is the separation medium is packed or filled into all the separation channels 12 by pressurizing by syringe from the anode side.

(3) Because the gel 22 flowing out from the separation channels 12 to the small-capacity reservoirs 14a disperses in the pure water of the large-capacity reservoir 16a, the water 20 and the gel 22 inside the reservoirs 14a, 16a are drawn by a suction nozzle, and the insides of the reservoirs 14a, 16a are cleaned.

Figure 4B:
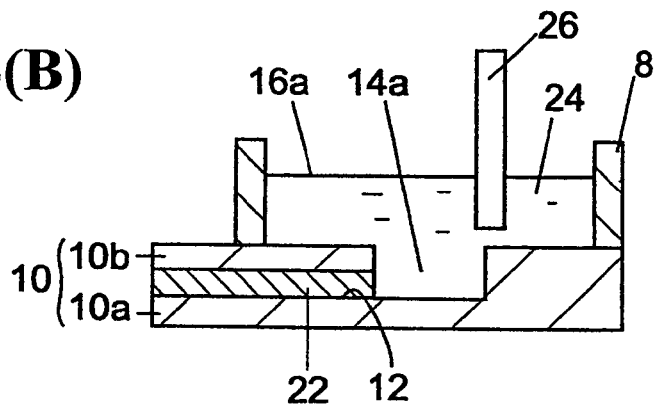

(4) After that, as shown in FIG. 4(B), buffer solution 24 maintained at room temperature is filled into the cathode-side reservoir 16a and the anode-side reservoir 16b, electrodes 26 are inserted into the buffer solution in both reservoirs 16a, 16b, and voltage is applied as preprocessing. By this preprocessing, ions of impurities in the gel 22 move toward the anode electrode or the cathode electrode. The applied voltage in this preprocessing is, for example, 125V/cm, and the application time is suitably 5 minutes.

(5) The buffer solution in the cathode-side reservoirs 14a, 16a is drawn, and the insides of the reservoirs 14a, 16a are cleaned, and then the insides of the reservoirs 14a, 16a are cleaned with pure water, for example Milli-Q water which is ultra-pure water.

Figure 4C:
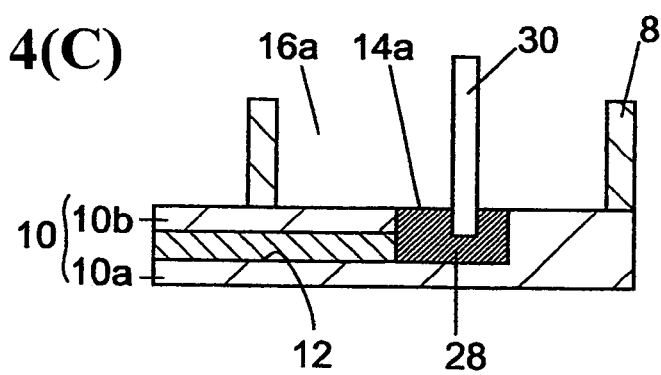

(6) After that, as shown in FIG. 4(C), a sample 28 is dripped into each small-capacity reservoir 14a.

(7) Next, a cathode electrode 30 is inserted into each small-capacity reservoir 14a, and voltage is applied between it and the anode electrode to perform sample injection into the channel 12. Numeral 11 is the injected sample. The applied voltage for sample injection is, for example, 50V/cm, and the application time is suitably 40 seconds.

Figure 4D:
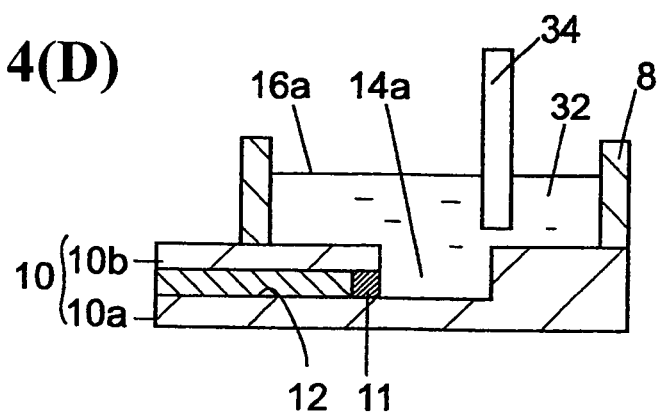

(8) After drawing and removing the sample remaining in the small-capacity reservoirs 14a, as shown in FIG. 4(D), the insides of the reservoirs 14a, 16a are filled with buffer solution 32.

(9) A cathode electrode 34 is inserted into the reservoir 16a, and running voltage is applied between it and the anode electrode immersed in the buffer solution of the reservoir 16b, and electrophoresis separation and signal detection of the sample are performed. The applied voltage for electrophoresis separation is suitably 70~300V/cm, for example, 125V/cm.

The electrode 26 for this electrophoresis separation may be provided in advance respectively in the reservoirs 16a, 16b. Also, the cathode electrode on the sample injection side may be provided in each small-capacity reservoir 14a.

Electrophoresis separation was performed respectively using three kinds of temperatures of the buffer solution 32 filled into the reservoirs 14a, 16a for electrophoresis separation, and the results were compared. Those three kinds of temperatures were 50° C. which is the same as the sample plate, 28° C. as that corresponding to room temperature, and 7° C. which is lower than those.

The measured sample was monobasic ladder DNA having a single base connected, and it was prepared using the BigDye v3.1 reagent kit for cycle sequencing (manufactured by Applied Biosystems Corporation). The template DNA was 0.5 μg/μL of pUC18 plasmid DNA (manufactured by Toyobo Corporation), and synthetic primer was used for the primer. The preparation conditions followed the kit handling instructions, and a standard product made by performing ethanol precipitation processing and then drying and hardening was obtained. Sample solution was prepared by dissolving that dry standard product using sample preparation solution containing each ingredient of 0.4 mM Tris-HCl (pH 8.0) and 0.04 mM 1.50% EDTA (w/v) ethylene glycol.

The results of separation performance of DNA performed under the above three kinds of buffer solution temperature conditions are shown in Table 5.

The horizontal axis is the base logarithm indicating the length of the DNA chain, and the vertical axis RI is the RI value indicating the separation performance. The RI value is defined by the following formula (see Non-Patent Document 1).

$$RI = 0.25 SN^{1/2}$$

$$S = 2|(tm1-tm2)/(tm1+tm2)|$$

$$N = 5.5(tm/W_{w0.5})^2$$

Here, tm1, tm2, tm, and $W_{w0.5}$ respectively are the mobility time of an arbitrary DNA chain, the mobility time of a DNA chain different from that, the mobility time of a certain DNA chain, and the half width of the peak when that DNA chain was detected.

Figure 5:
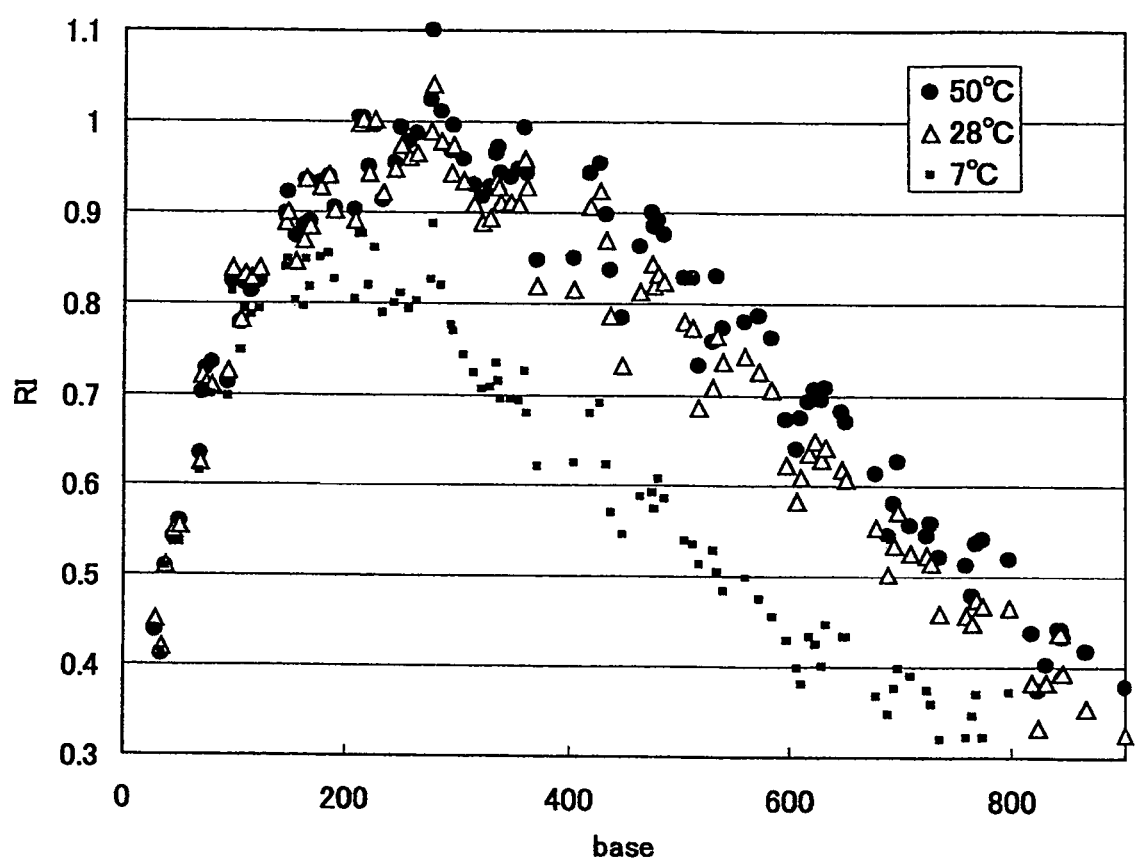
FIG. 5 is a graph showing one example of the results of electrophoresis separation.

According to the results in FIG. 5, when buffer solution at room temperature (28° C.) was injected as in the past, it was subject to the influence of external atmospheric temperature, and when that buffer solution temperature was lowered further (7° C.), the separation performance was lowered further. As opposed to that, when the buffer solution temperature was made 50° C. which is the same as the sample plate according to the present invention, the separation performance in macromolecular DNA having 400 bases or more was improved.

In the working example, the temperature of the buffer solution injected during preprocessing was made at room temperature, but the separation performance can be improved further by using the same temperature as the sample plate also for that buffer solution temperature.

Figure 6A:
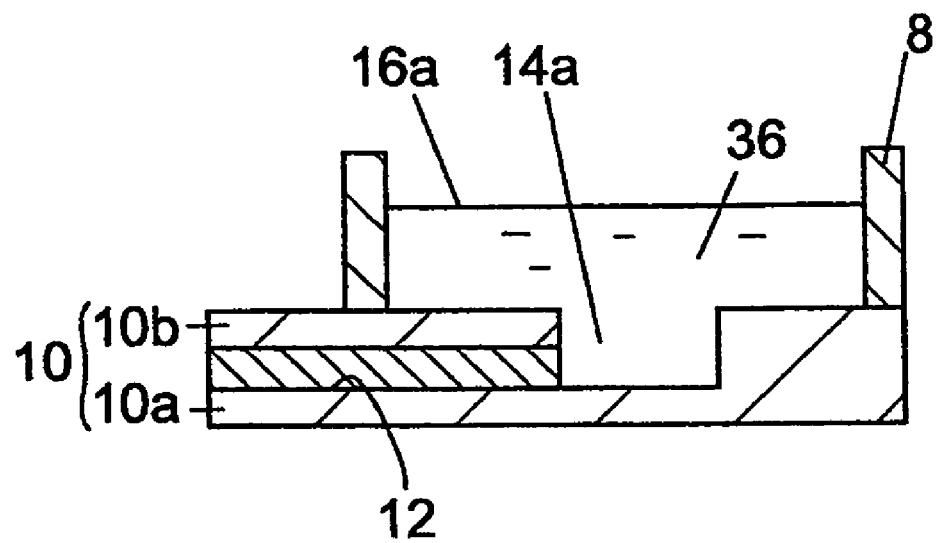
FIGS. 6(A) and 6(B) are sectional views of the process showing the course of sample injection in another working example.
Figure 6B:
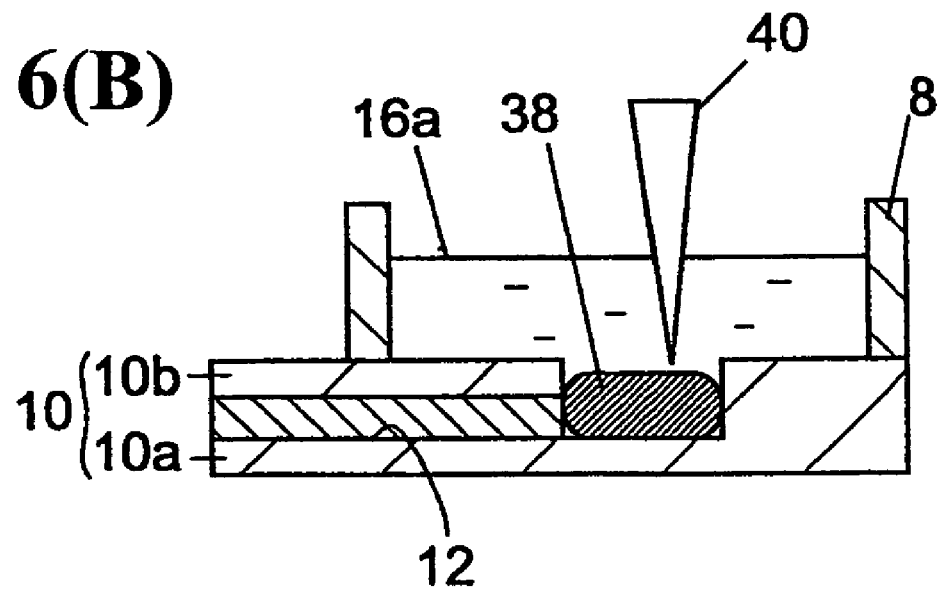

In the working example, sample injection was performed in a state that the reservoirs 14a, 16a are empty as shown in FIG. 4(C). However, since the sample plate is maintained in the specific temperature, it is preferable to consider a measure for preventing drying of the sample. For example, the reservoirs 14a, 16a may be filled with pure water 36 as shown in FIG. 6(A), and with the sample 38 in a state being dissolved in a medium having greater specific gravity than water, it may be injected by pipette 40, or the like, as shown in FIG. 6(B).

As such medium having greater specific gravity for dissolving the sample, a liquid having low viscosity and tending not to volatize is preferable. For example, at least one compound selected from a group consisting of polyvalent alcohols, sugars, and other hydrophilic polymer compounds, consisting mainly of water can be included. As polyvalent alcohols, divalent alcohols and trivalent alcohols, for example, ethylene glycol, glycerol, pentaerythritol, propylene glycol, and mannitol, and the like, can be mentioned. As sugars, monosaccharides, and oligosaccharides and polysaccharides having plural of these condensed, are included, concretely, glucose and sucrose, dextrolan, and the like, can be mentioned.

The sample injection method of the present invention can be used in the fields such as biochemistry, molecular biology or clinical practice.

The disclosure of Japanese Patent Application No. 2005-065547 filed on Mar. 9, 2005 is incorporated herein.

While the invention has been explained with reference to the specific embodiments of the invention, the explanation is illustrative, and the invention is limited only by the appended claims.

What is claimed is:

1. An electrophoresis method, comprising:
preparing a capillary plate having plural capillary channels, one common reservoir provided on a sample injection side of the plural capillary channels, and small reservoirs provided at a bottom of the one common reservoir and communicating with the respective capillary channels, maintaining the capillary plate having the capillary channel at a predetermined temperature to be processed, filling samples into the small reservoirs, preparing a solution having a solution temperature which is controlled to be at most ±5 degrees of the predetermined temperature of the capillary plate, injecting the solution into the common reservoir maintained at the predetermined solution temperature, and applying voltage between two ends of the capillary channel to perform electrophoresis of the sample.

2. An electrophoresis method according to claim 1, further comprising the step of providing a separation medium into the capillary channels before the samples are filled into the capillary channels.

3. An electrophoresis method according to claim 2, further comprising a preprocessing after providing of the separation medium into the capillary channels and before filling the samples.

4. An electrophoresis method according to claim 3, wherein said preprocessing comprises the step of injecting a preprocessing solution maintained substantially at the predetermined temperature of the capillary plate into common reservoir, and the step of applying voltage between two ends of the capillary channel.

5. An electrophoresis method according to claim 1, wherein the solution has the solution temperature which is controlled within ±2.5 degrees of the predetermined temperature of the capillary plate.

* * * * *